United States Patent [19]

Hausheer

[11] Patent Number: 6,034,126

[45] Date of Patent: Mar. 7, 2000

[54] METHOD FOR TREATING GLYCOL POISONING

[75] Inventor: Frederick Herman Hausheer, Boerne, Tex.

[73] Assignee: BioNumerik Pharmaceuticals, Inc., San Antonio, Tex.

[21] Appl. No.: 09/317,693

[22] Filed: May 24, 1999

[51] Int. Cl.[7] .................. A61K 31/185; A61K 31/28; A61K 31/255; A61K 31/66

[52] U.S. Cl. .................. 514/517; 514/108; 514/127; 514/492; 514/578

[58] Field of Search .................................. 514/108, 127, 514/517, 578, 492

[56] References Cited

U.S. PATENT DOCUMENTS

| 4,218,471 | 8/1980 | Brock et al. | 424/315 |
|---|---|---|---|
| 5,789,000 | 8/1998 | Hausheer et al. | 424/649 |
| 5,902,610 | 5/1999 | Hausheer et al. | 424/649 |
| 5,919,816 | 7/1999 | Hausheer et al. | 514/449 |

OTHER PUBLICATIONS

Eder et al., Clinical Chemistry, 44(1), pp. 168–177 (abstract), Jan. 1998.

*Primary Examiner*—Phyllis G. Spivack
*Attorney, Agent, or Firm*—Thomas J. Dodd

[57] ABSTRACT

This invention relates to a method of treating patients afflicted with glycol poisoning. The method includes administering to a patient in need of treatment an antidotal amount of a thiol or reducible disulfide compound according to the formula set forth in the specification.

6 Claims, No Drawings

METHOD FOR TREATING GLYCOL POISONING

FIELD OF THE INVENTION

This invention relates to a method for treating a patient suffering from glycol poisoning. The method involves administering an antidotal amount of a disulfide or thiol-containing compound to a patient suffering from glycol poisoning.

BACKGROUND OF THE INVENTION

Glycol poisoning, particularly ethylene glycol poisoning, is a serious, often fatal condition, even with the currently available treatment. Glycol poisoning is common among children and animals in particular, due to its presence in high concentrations in automobile antifreeze and other common household products. An unknowing child or animal accidentally drinks the glycol containing liquid usually because of its sweet odor and taste, and unless treatment is begun promptly after ingestion, permanent damage or death will result depending on the amount ingested. The main organs affected by glycol metabolites are the kidneys, liver, central and peripheral nervous systems, lungs, and others. Many effects of glycol poisoning are reversible, particularly if treatment is begun soon after intoxication.

Current antidotes/treatments for glycol poisoning are limited. Generally, ethyl alcohol is administered to the patient in order to impede the conversion of ethylene glycol to its highly toxic oxalate metabolites. Therapy is continued until the patient's blood glycol levels are reduced to non-dangerous levels.

The obvious drawback of this therapy is that ethyl alcohol is itself converted to toxic metabolites, and its use must be strictly monitored to avoid alcohol poisoning. In addition, the patient being treated remains in a state of alcohol intoxication throughout the therapy, hardly a desirable condition.

Recently, a new non-alcohol agent, 4-methyl pyrazole (4-MP, fomepizole, Antizol®), has been approved for use as a glycol poisoning antidote. Like ethyl alcohol, 4-MP retards the formation of the toxic oxalate metabolites by competitive antagonization of alcohol dehydrogenase. 4-MP is many times more expensive than ethyl alcohol, but much safer to use.

Mesna (sodium 2-mercaptoethene sulfonate) and dimesna (disodium 2,2'-dithiobis ethane sulfonate) are known therapeutic compounds which have heretofore demonstrated a wide variety of therapeutic uses. Both mesna and dimesna have been shown to be effective protective agents against certain specific types of toxicity associated with the administration of cytotoxic drugs used to treat patients for various types of cancer. In particular, mesna has been used with some success in mitigating the toxic effects of cytotoxic agents such as ifosfamide, oxazaphosphorine, melphalane, cyclophosphamide, trofosfamide, sulfosfamide, chlorambucil, busulfan, triethylene thiophosphamide, triaziquone, and others, as disclosed in U.S. Pat. No. 4,220,660, issued Sep. 2, 1980.

The near absence of toxicity of dimesna further underscores the usefulness of this compound, as large doses that may be needed can be given to a patient without increasing the risk of adverse effects from the protective agent itself.

Further, pharmacological profiles of each compound indicate that, if proper conditions are maintained, mesna and dimesna do not prematurely inactivate primary therapeutic drugs to a significant degree. Thus, neither compound will significantly reduce activity of the chemotherapeutic agent, and in many cases, act to potentiate the effect of the main drug on targeted cancer cells.

The structures of both mesna and dimesna are shown below as Formula I and Formula II respectively.

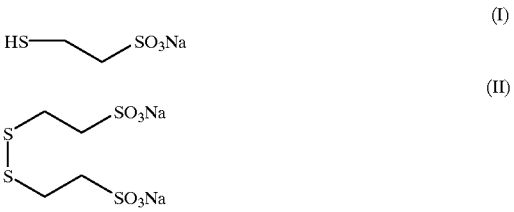

As is well known, dimesna is a dimer of mesna, with the optimum conditions for oxidation occurring in the slightly basic (pH ~7.3), oxygen rich environment found in blood plasma. In mildly acidic, low oxygen conditions, in the presence of a reducing agent such as glutathione reductase, conditions prevalent in the kidneys, the primary constituent is mesna.

Mesna acts as a protective agent for a number of cytotoxic agents by substituting a nontoxic sulfhydryl moiety for a toxic hydroxy (or aquo) moiety. This action is particularly evidenced in the coadministration of mesna and oxazaphosphorine, and in the administration of dimesna along with cisplatin or carboplatin.

Mesna and dimesna, as well as some analogues of these compounds, have excellent toxicity profiles in mammalian species. In fact, dimesna has been administered intravenously to rats and dogs in doses higher than the accepted oral $LD_{50}$ for common table salt (3750 mg/kg), with no adverse effects. Dimesna has also been administered to humans in doses exceeding 25 g/m$^2$ with no adverse effects.

Mesna, and other analogues with free thiol moieties, constitute the more physiologically active form of the two types of compounds described in this specification. These compounds manifest their activity by providing free thiol moieties for terminal substitution at locations where a terminal leaving group of appropriate configuration is located.

Dimesna and other disulfides can be activated intracellularly by glutathione reductase, a ubiquitous enzyme, thereby generating high concentrations of intracellular free thiols. These free thiols act to scavenge the free radicals and other nucleophilic compounds often responsible for causing cell damage.

This profile is especially significant in explaining the success of dimesna in controlling and mitigating the toxic effects of platinum complex antitumor drugs. The mechanism for action in the case of cisplatin (cis-diammine dichloro platinum) is explained in U.S. Pat. No. 5,789,000, which is incorporated herein by reference.

Mesna, dimesna, and analogues of these compounds have been the subject of several prior pharmaceutical uses described in the literature and in prior patents, both in the United States and around the world. In addition to the cytotoxic agent protection uses, one or more of these compounds have proven effective, in vitro, against a multiplicity of biological targets, and have been effective, in vivo, in the treatment of sickle cell disease, radiation exposure, chemical agent exposure, and other uses.

Mesna, dimesna, and analogues thereof are synthesized from commonly available starting materials, using acceptable routes well-known in the art. One such method involves the two-step, single pot synthetic process for making dimesna and like compounds of the following formula:

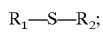

wherein:
R$_1$ is hydrogen, X-lower alkyl, or X-lower alkyl-R$_3$;
R$_2$ is -lower alkyl-R$_4$;
R$_3$ and R$_4$ are each individually SO$_3$M or PO$_3$M$_2$;
X is absent or X is sulfur; and
M is an alkali metal.

The process essentially involves a two step single pot synthetic process which results in the conversion of an alkenyl sulfonate salt or acid to the desired formula I compound. The process in the case of mesna is a single step process which converts the alkenyl sulfonate salt to mesna or a mesna derivative by reacting with an alkali metal sulfide or with hydrogen sulfide.

If the desired end product is dimesna or a dimesna analogue, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C. Dimesna or a derivative thereof is formed in essentially quantitative yield.

Other processes, well-known and documented in the prior art, may be employed to make either mesna or dimesna, or derivatives and analogues thereof.

SUMMARY OF THE INVENTION

This invention involves the administration of antidotal amounts of compounds of formula I, below, for treating patients afflicted with glycol poisoning.

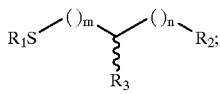

wherein:
R$_1$ is hydrogen, lower alkyl or

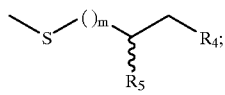

R$_2$ and R$_4$ are each individually SO$_3^-$M$^+$, PO$_3^{2-}$M$_2^{2+}$, or PO$_2$S$^{2-}$M$_2^{2+}$;
R$_3$ and R$_5$ are each individually hydrogen, hydroxy or sulfhydryl;
m and n are individually 0, 1, 2, 3 or 4, with the proviso that if m or n is 0, then R$_3$ is hydrogen; and
M is hydrogen or an alkali metal ion; or
a pharmaceutically acceptable salt thereof.

Effective amounts of the formula I compounds to be administered according to the method of this invention vary, and depend on the severity and duration of the glycol poisoning.

Accordingly, it is an object of this invention to provide for a method of safely and effectively treating glycol poisoning.

Another object is to provide a method of treating glycol poisoning by administration of a thiol or reducible disulfide to the patient in need of treatment.

Other objects will become apparent upon a reading of the following description.

DESCRIPTION OF THE PREFERRED EMBODIMENTS

The preferred embodiments herein described are not intended to be exhaustive nor to limit the invention to the precise form disclosed. They are chosen and described to explain the principles of the invention, and its application and practical use to best enable others skilled in the art to follow its teachings.

The method of this invention involves the administration of an effective amount, also referred to as an antidotal amount, of a formula I compound to a patient suffering from glycol poisoning. Administration may be either oral or parenteral.

The effective amount of the formula I compound will necessarily depend upon the degree of the poisoning. Since the formula I compounds are essentially nontoxic, large amounts can be safely administered. The preferred dosage to treat glycol poisoning ranges from an equimolar amount of the formula I compound when compared to the blood levels of the glycol, up to several thousand times the amount of the glycol.

Normally, the effective amount to be administered ranges from 0.1 mg/kg of body weight up to 1,000 mg/kg. The more severe the poisoning, the more formula I compound should be administered to provide an antidotal response.

The method is effective against glycol poisonings which include ethylene glycol, propylene glycol and others.

Administration is preferably through parenteral or oral routes. For parenteral administration, the formula I compound is dissolved in a suitable solvent, most preferably water, to produce a solution which may be injected. One or more pharmaceutically acceptable excipients may also be added to provide for an elegant formulation.

For oral administration the formula I compound is preferably combined with one or more pharmaceutically acceptable excipients, fillers and/or diluents. Oral dosage forms may include pills, caplets, tablets, and others. Alternatively, the formula I compound may be contained in a swallowable container such as a gelatin capsule or the like.

The formula I compounds work to detoxify the glycol complexes by substituting a thiol moiety for a hydroxy or aquo moiety in the glycol metabolites. This substitution renders the glycol relatively nontoxic, and increases the water solubility, which both impedes entry into cells and facilitates elimination through the kidneys.

Administration of the formula I compound should be made as soon as possible following diagnosis of glycol poisoning. Preferred initial dose is between 10 g/m$^2$ to 25 g/m$^2$. Careful observation and blood analysis is performed regularly after diagnosis as per accepted medical procedures for treating glycol poisoning. Repeat doses of the formula I compound are administered as needed until the blood glycol levels are reduced to levels deemed nontoxic.

Other accepted methods of treatment may also be combined with the administration of the formula I compound. In particular, if the poisoning is recent in nature, emesis-inducing drugs, or ethanol, or 4-MP may be administered in conjunction with the formula I compound.

It is understood that the above description is in no way limiting of the invention, which may be modified within the scope of the following claims.

What is claimed is:

1. A method of treating a patient afflicted with glycol poisoning, said method comprising administering an antidotal amount of a compound of formula I:

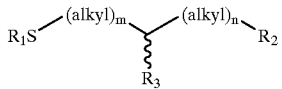
(I)

wherein:

$R_1$ is hydrogen, lower alkyl or

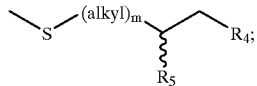

$R_2$ and $R_4$ are each individually $SO_3^-M^+$, $PO_3^{2-}M_2^{2+}$, or $PO_2S^{2-}M_2^{2+}$;

$R_3$ and $R_5$ are each individually hydrogen, hydroxy or sulfhydryl;

m and n are individually 0, 1, 2, 3 or 4, with the proviso that if m or n is 0, then $R_3$ is hydrogen; and M is hydrogen or an alkali metal ion; or a pharmaceutically acceptable salt thereof.

2. The method of claim 1 wherein the antidotal amount of the formula I compound administered is from 0.1 mg/kg of body weight to 1,000 mg/kg of body weight.

3. The method of claim 1 wherein the compound is administered orally.

4. The method of claim 1 wherein the compound is administered parenterally.

5. The method of claim 1 wherein the compound is administered prior to, simultaneously with, or following the administration of emesis-inducing agents.

6. The method of claim 2 wherein the antidotal amount is from 1 to 1,000 times the molar amount of the glycol found in the bloodstream.

* * * * *